(12) United States Patent
Kropp et al.

(10) Patent No.: US 7,875,276 B2
(45) Date of Patent: *Jan. 25, 2011

(54) URINARY TRACT TISSUE GRAFT COMPOSITIONS AND METHODS FOR PRODUCING SAME

(75) Inventors: Bradley Kropp, Edmond, OK (US); Earl Y. Cheng, Elmhurst, IL (US); Yuan Yuan Zhang, Edmond, OK (US); Hsueh-Kung Lin, Edmond, OK (US); Rick Cowan, Oklahoma City, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 752 days.

This patent is subject to a terminal disclaimer.

(21) Appl. No.: 11/799,926

(22) Filed: May 3, 2007

(65) Prior Publication Data

US 2007/0218040 A1 Sep. 20, 2007

Related U.S. Application Data

(60) Division of application No. 10/631,168, filed on Jul. 31, 2003, now Pat. No. 7,344,712, which is a continuation-in-part of application No. 10/314,799, filed on Dec. 6, 2002, now Pat. No. 7,078,033, which is a continuation-in-part of application No. 10/013,270, filed on Dec. 10, 2001, now Pat. No. 7,122,200.

(60) Provisional application No. 60/400,401, filed on Jul. 31, 2002, provisional application No. 60/254,186, filed on Dec. 8, 2000.

(51) Int. Cl.
*C12N 5/00* (2006.01)
(52) U.S. Cl. ...................................... 424/93.7; 435/373
(58) Field of Classification Search .................. 435/373; 424/93.7
See application file for complete search history.

(56) References Cited

U.S. PATENT DOCUMENTS

| | | | |
|---|---|---|---|
| 5,695,998 A | 12/1997 | Badylak et al. | |
| 5,762,966 A | 6/1998 | Knapp, Jr. et al. | |
| 5,866,414 A | 2/1999 | Badylak et al. | |
| 6,576,265 B1 | 6/2003 | Spievack | |
| 7,078,033 B2 * | 7/2006 | Kropp et al. | 424/93.7 |
| 7,122,200 B2 | 10/2006 | Kropp et al. | |
| 7,344,712 B2 * | 3/2008 | Kropp et al. | 424/93.7 |
| 2002/0155096 A1 | 10/2002 | Chancellor et al. | |
| 2003/0216811 A1 | 11/2003 | Badylak | |

OTHER PUBLICATIONS

Zhang et al.; "'Co-Culture' of Bladder Smooth Muscle and Urothelial Cells on Small Intestinal Submococa (sis): Evaluation of the Best Culture Method for In Vitro Tissue Engineering Techniques"; Pediatrics Journal Supp: Sep. 1999:807-808.

Zhang, Y. et al.; "Coculture of Bladder Urothelila and Smooth Muscle Cells on Small Intestinal Submucosa: Potential Applications for Tissue Engineering Technology"; Journal of Urology 164:928-935 (2000).

Lu et al.; "Muscle-Derived Stem Cells Seeded Into Acellular Scaffolds Develop Calcium-Dependent Contractile Activity That Is Modulated by Nicotinic Receptors"; Urology 61:1285-1291, 2003.

* cited by examiner

*Primary Examiner*—Ruth A Davis
(74) *Attorney, Agent, or Firm*—Dunlap Codding, P.C.

(57) ABSTRACT

A method for providing a urinary tract tissue graft composition includes providing a segment of small intestinal submucosa and isolating and culturing at least one multipotent cell type from a tissue specimen of a subject. The at least one multipotent cell type is then seeded upon a surface of the segment of small intestinal submucosa and allowed to differentiate into a unipotent cell type, thereby forming a urinary tract tissue graft. Methods for repairing a damaged urinary tract tissue of a subject are also disclosed.

6 Claims, 11 Drawing Sheets
(8 of 11 Drawing Sheet(s) Filed in Color)

Figure 6
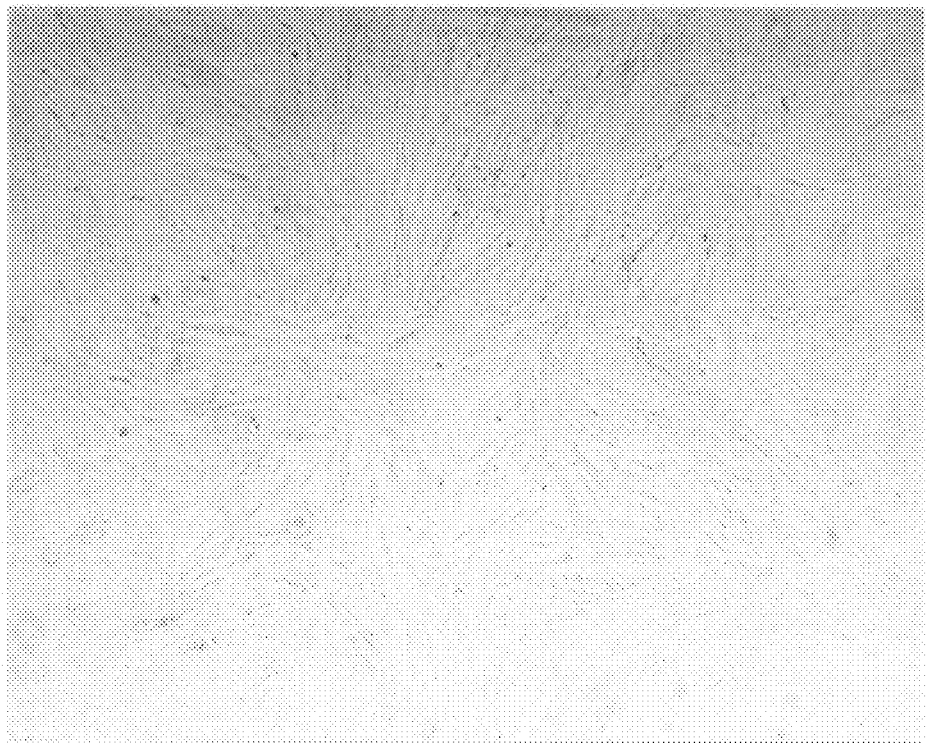
A
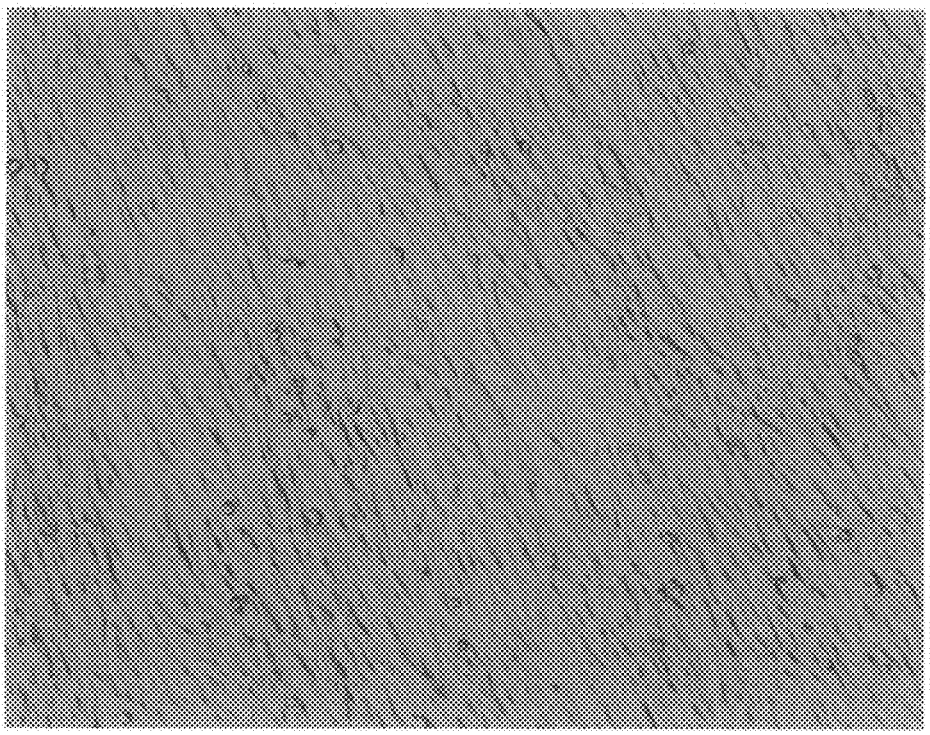
B

Figure 11
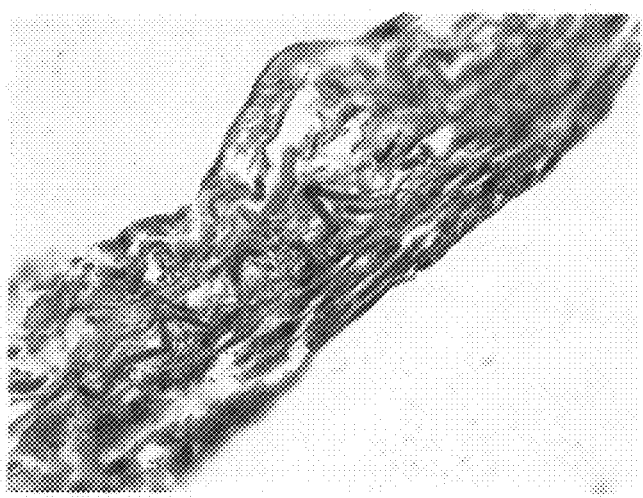
A
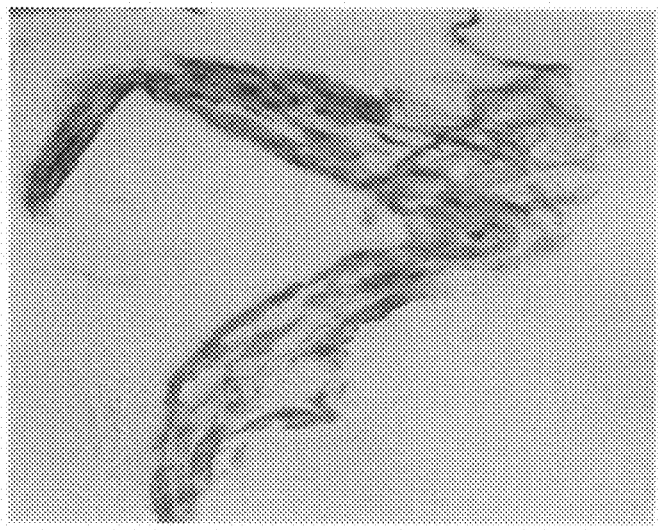
B
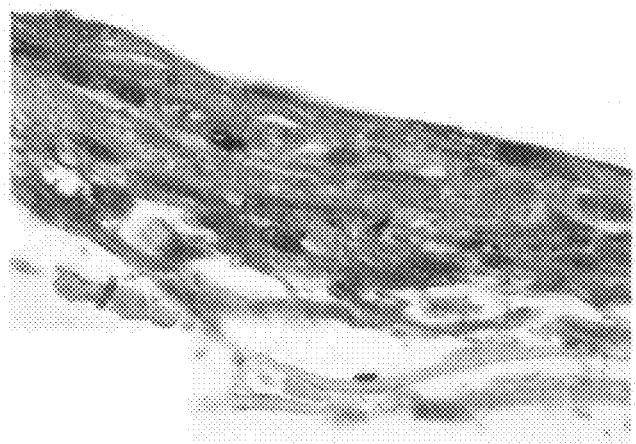
C

URINARY TRACT TISSUE GRAFT COMPOSITIONS AND METHODS FOR PRODUCING SAME

CROSS-REFERENCE TO RELATED APPLICATIONS

This application is a divisional of U.S. Ser. No. 10/631,168, filed Jul. 31, 2003; now U.S. Pat. No. 7,344,712 which claims benefit under 35 U.S.C. 119(e) of U.S. Provisional Application Ser. No. 60/400,401, filed Jul. 31, 2002.

Said application U.S. Ser. No. 10/631,168 is also a continuation-in-part of U.S. Ser. No. 10/314,799, filed Dec. 6, 2002, now U.S. Pat. No. 7,078,033, issued Jul. 18, 2006; which is a continuation-in-part of U.S. Ser. No. 10/013,270, filed Dec. 10, 2001, now U.S. Pat. No. 7,122,200, issued Oct. 17, 2006; which claims benefit under 35 U.S.C. 119(e) of U.S. Ser. No. 60/254,186, filed Dec. 8, 2000.

FEDERALLY SPONSORED RESEARCH OR DEVELOPMENT

This Invention was made with government support under Grant No. DK056968 awarded by the National Institutes of Health. The government has certain rights in the invention.

The entire contents of each of the above-referenced patents and applications are hereby expressly incorporated herein by reference.

BACKGROUND OF THE INVENTION

1. Field of the Invention

The present invention relates to methods of tissue reconstruction and repair, and more particularly, but not by way of limitation, to seeded tissue engineering techniques, as well as tissue grafts formed by such methods.

2. Brief Description of the Related Art

At least twenty-five percent of the clinical problems in pediatric urology are caused by neurologic lesions that affect lower urinary tract function. These clinical presentations are highlighted by urinary incontinence, urinary tract infections and decreased bladder compliance that leads to increased pressure transmission to the upper urinary tract which leads to subsequent renal deterioration. The monetary cost to our health care system of treating children with dysfunctional bladders runs into millions of dollars each year. Therefore, the need for bladder augmentation has increased in both the adult and pediatric population. This increased need requires surgical techniques that are clinically and socially acceptable and allow these children and adults to live a healthier and more normal life. The current methods of treatment of bladder dysfunction leave those goals largely unmet and must be improved if we hope to improve the prognosis of this large population of urology patients.

The gastrointestinal tract has been the autologous tissue source of choice for genitourinary reconstruction in both the adult and pediatric population. Deleterious side effects associated with the use of bowel include infection, intestinal obstruction, mucus production, electrolyte abnormalities, perforation and neoplasia. These potential side effects have ignited tissue engineering research involving bladder reconstruction through bladder regeneration. These endeavors have shown that there is an urgent need for the development of biodegradable materials with predictable behavior and well characterized mechanical properties that can be used as alternatives to gastrointestinal segments for bladder reconstruction. One major obstacle to advancing the field of urinary tract reconstruction and rehabilitation has been the availability of a biomaterial, either permanent or biodegradable, that will function as a suitable scaffold to allow the natural process of regeneration to occur. The ideal graft material would be replaced by the host tissue, promote the development of a structurally intact low pressure reservoir, and serve as a scaffold for the healing and regeneration of the bladder wall. If a suitable exogenous graft material was available, the need for autogenous tissue and all of the negative consequences associated with its harvest could be eliminated. Therefore, investigators continue to search for the proper scaffold and methodology that is necessary to regenerate tissue and maximally restore urinary tract function. Currently, two technologies involving tissue engineering for bladder regeneration and augmentation are being investigated.

The first reconstructive technology, the in vivo or unseeded tissue engineering technique for bladder regeneration, employs xenogenic (derived from stomach, bladder or small intestine) or synthetic biodegradable, acellular matrices. This tissue engineering technique involves the direct in vivo placement of an unseeded biodegradable material into a host that will then function as a scaffold to allow the natural process of regeneration to occur. While this technology provides the scaffold for wound healing and tissue regeneration, it also requires the host to provide the tissue and proper environment for cell growth and tissue regeneration.

There are two major obstacles for in vivo or unseeded tissue engineering technology for bladder regeneration. The first has been finding a biomaterial that will act as a suitable scaffold for this natural process to occur. Synthetic non-biodegradable biomaterials such as silicone, rubber, polytetrafluoroethylene, and polypropylene have been unsuccessful because of mechanical failure, lithogenesis, or host foreign body reactions (see, e.g., Kudish, H. G., *J. Urol.* 78:232 (1957); Ashkar, L. and Heller, E., *J. Urol.* 98:91 (1967); Kelami et al., *J. Urol.* 104:693 (1970); the contents of each of which are hereby expressly incorporated by reference in their entirety). As a consequence of failures with non-biodegradable materials, synthetic biodegradable materials have been investigated that would allow the host bladder time for regeneration but then dissolve prior to the onset of any foreign body reaction. These materials have been applied experimentally and have shown improvement over non-biodegradable materials. Xenogenic, collagen-rich biodegradable materials such as placenta, amnion and pericardium have been used with even more encouraging experimental results than studies employing non-biodegradable synthetic materials. However, despite initial encouraging results, none of these materials have been found to be suitable for clinical use. It has been reported that bladders augmented with dura, peritoneum, placenta and fascia contract over time, and that such tissue grafts fail to promote complete bladder wall regeneration (i.e., tissue having a urine impermeable layer and a functional muscle cell layer) (Kelami, et al., *J. Urol.* 105:518 (1971)).

The second potential limitation of the unseeded tissue engineering technique for bladder regeneration is that the size of the graft may be limited to the amount of area which can be quickly invested with bladder cells from the remaining native bladder, and therefore may not be sufficient for bladder replacement. If the ratio of the size of the unseeded graft to the amount of native bladder tissue becomes too large, the ability of the animal to invest the graft with smooth muscle cells (SMC) and urothelial cells (UC) appears to be compromised. In the absence of quickly covering the graft with bladder cells, contraction and excess scar formation becomes a concern and poor clinical outcomes may result.

Clearly a tissue graft material is desired which is non-immunogenic, not subject to gross shrinkage after implantation, and which promotes the growth of endogenous urinary bladder tissues having a urine impermeable cell layer and a functional muscle cell layer. A collagen-based biomaterial called small intestinal submucosa (SIS) is a xenogenic membrane harvested from small intestine (such as pig small intestine) in which the tunica mucosa is mechanically removed from the inner surface, and the serosa and tunica muscularis are mechanically removed from the outer surface. This produces a thin, translucent graft (0.1 mm wall thickness) composed mainly of the submucosal layer of the intestinal wall. The submucosal layer of animal intestine has an established background in surgery as gut suture. This collagen-rich membrane has been previously shown to function well as an arterial or venous graft eliciting rapid replacement by native tissues. For example, U.S. Pat. No. 4,902,508, issued to Badylak et al. on Feb. 20, 1990, and U.S. Pat. No. 4,956,178, issued to Badylak et al. on Sep. 11, 1990, the contents of which are hereby expressly incorporated herein by reference in their entirety, describe SIS autografts and allografts prepared from the upper jejunum of a dog and used beneficially for vascular constructs.

SIS has also been shown to have excellent host compatibility and remodeling when submucosal bladder injections of minced SIS were performed in pigs (see U.S. Pat. No. 5,275,826, issued Jan. 4, 1994, to Badylak et al., the contents of which are hereby expressly incorporated herein by reference). To date, SIS has been shown to be non-immunogenic with over 1,000 cross-species transplants and direct challenge testing, demonstrating the lack of immunogenicity thereof. Additionally, SIS has been shown to contain a combination of active intrinsic growth factors, cytokines, structural proteins, glycoproteins and proteoglycans that may assist in cell migration and cell to cell interaction as well as cell growth and differentiation during the regenerative process. Based upon these highly desirable characteristics, it appears that SIS has potential as a universal tissue graft.

Initial research using SIS for urinary bladder augmentation was performed in a rat model, and SIS was shown to function as a scaffold to allow the native rat bladder to remodel and regenerate itself. Histologically, the regenerated rat bladders contained all three layers of the bladder (urothelium, smooth muscle and serosa) and were indistinguishable from normal rat bladder at 11 months post-augmentation (Kropp et al., *Urology* 46:396 (1995)). In addition, in vitro contractility studies showed that strips of in vivo tissue engineered SIS-regenerated rat bladder had contractile properties and nerve regeneration that was similar to the normal rat bladder (Vaught et al., *J. Urol.* 155:374 (1996)). This was the first evidence that a functional bladder could be achieved with tissue engineering techniques. It also demonstrated that SIS was different than other biomatrix materials that have been studied in the past. Previously, no other material had shown the ability to promote the regenerative capacity of bladder tissue that SIS was demonstrating in the small animal model.

A long term, large animal model evaluating in vivo tissue engineering of SIS bladder augmentation, in which 40% of a canine bladder was removed and replaced with a similar size piece of SIS, demonstrated that the regenerated bladder remained urodynamically compliant with similar capacities as control dogs. There were no deleterious side effects or upper tract changes up to 15 months post-augmentation. Gross examination revealed that all three layers of the bladder had regenerated. However, the quantity and organization of smooth muscle fibers differed slightly from the normal bladder (Kropp et al., *J. Urol.* 155:2098 (1996)). In vitro contractility bladder strip studies performed on the SIS-regenerated portions of the bladder demonstrated contractile activity and expression of muscarinic, adrenergic and purinergic receptors similar to normal bladder. As was the case in the rat model, SIS-regenerated bladder also demonstrated functional nerve regeneration and innervation that is similar to normal bladder. Finally, in vitro stress/strain compliance studies demonstrated no significant difference between SIS-regenerated bladder and control bladder, both of which were 30-fold more compliant than the original SIS graft material (Kropp et al., *J. Urol.* 156:599 (1996)).

Critical histological analysis of the regenerated bladder tissue has revealed that the collagen-to-muscle ratio is increased in small intestinal submucosa regenerated bladder compared to normal bladder and that the degree of regeneration is variable within a given graft. The clinical and functional implications of these findings are not clear. In addition, while the obstacle of identifying a biomaterial that will act as a suitable scaffold for the natural process of bladder regeneration to occur is overcome by the use of SIS in unseeded tissue engineering technology, the obstacle of the limited size of a graft formed therefrom still exists.

The second tissue reconstruction technology, the in vitro or seeded tissue engineering technique, utilizes biodegradable materials that serve as both a scaffold for the regeneration process to occur as well as cell-delivery vehicles. This technology involves initial harvesting of bladder tissue, such as from a biopsy from host native tissue, to establish primary cultures of bladder cells. Cilento et al. (*J. Urol.* 152:665 (1994)) demonstrated that it is theoretically possible to expand a transitional epithelial strain to cover the area of an entire football field using this method of cell culture. These cells are then seeded on a biodegradable membrane and, following a period of graft maturation, the in vitro created bladder graft is then transplanted back into the host for continuation of the regeneration process.

In 1992, Atala et al. (*J. Urol.* 148:658 (1992)) demonstrated the successful use of non-woven polyglycolic acid polymers (PAP) to facilitate the in vitro growth of rabbit and human bladder epithelium and smooth muscle cells. They further demonstrated that human transitional epithelium and smooth muscle cells grown on the biodegradable polymers could then be implanted into athymic mice and grown in vivo, and that the tissue architecture became progressively more complex with time in the animal.

Recently, Yoo et al. (*Urology* 51:221 (1998)) and Oberpenning et al. (*Nat. Biotechnol.* 17:149 (1999)) reported on the feasibility of dog bladder augmentation using allogenic bladder submucosa and PAP membranes seeded with urothelial and smooth muscle cells. This study demonstrated that transitional epithelium and smooth muscle cells could be harvested, grown and subsequently seeded on allogenic bladder submucosa for use as augmentation material. Urodynamically, the augmented bladder demonstrated increased capacity during this short term study. Interestingly, the allogenic bladder submucosa which was unseeded also demonstrated the ability to increase bladder capacity, however the gains in capacity were less than the seeded grafts. Studies such as this as well as those of Atala et al. suggest that prior cell seeding of large bladder grafts may be necessary to obtain the best clinical outcome following bladder augmentation. Unfortunately, although the in vitro technique of tissue engineering has been shown to be feasible for both synthetic and xenogenic matrices, thus far no studies have been undertaken to determine the effectiveness of the materials to facilitate the regeneration of functional bladder tissue in a large animal.

In addition, while all segments of small intestinal submucosa have been used to promote urinary bladder regeneration, multiple problems have been encountered with different small intestinal segments, including calcifications and graft shrinkage, and therefore unreliable and inconsistent results have been obtained in the experimental use of this material for bladder augmentation. However, thus far no studies have been undertaken to determine if the effectiveness of one segment of small intestine over another and to determine if the use of one segment of small intestine over another has any effect on the consistency and reliability of the grafts formed therefrom.

Another disadvantage associated with current seeded tissue engineering techniques for bladder reconstruction is that it utilizes bladder tissue collected from the host. In reality, healthy native bladder tissues may not be available for this purpose due to scarring, disease or malignancy. In other cases, the available native bladder tissue might not be an ideal cell source for tissue engineering, as it would result in the regeneration of a sub-functional or even non-functional bladder. For example, patients with neuropathic bladders have non-functional bladder tissue with severe inflammatory and intense fibrosis formation. Recently, it has been demonstrated that neuropathic bladder smooth muscle cells (SMC) have certain characteristics which are significantly different from normal bladder SMC, including less cell adhesion, less contractility and rapid cell proliferation (Cheng et al., *American Academic Pediatrics*, 1999). There is a serious concern in the use of native dysfunctional cell sources for bladder reconstruction, and a need exists for alternative cell sources for use in tissue engineered bladder regeneration.

Stem cells are a type of "master cell" that could be a great source for the replacement of damaged or diseased tissues. There are two types of stem cells: embryonic stem cells and specific cell types derived from adult tissues, including blood from the umbilical cords of newborns, peripheral blood, bone marrow, foreskin and skeletal muscle cells. Previous studies demonstrated that stem cells were primordial cells and had the capacity to differentiate into many different cell types including bone, neurons, heart, and liver tissue in both in vitro and in vivo settings. The differentiation potential of these cells has created a great deal of excitement in the field of tissue engineering, since stem cells can provide a resource for replacing diseased cells for regenerating purposes.

Embryonic stem cells (ESC) are pluripotent cells which are derived from the inner cell mass of a blastocyst. The unique characteristics of ESC are their capacities to regenerate themselves and to be capable of developing into various cell types of all three embryonic germ layers, ectoderm, mesoderm and endoderm, under appropriate environments. Such differentiated cell types include, but are not limited to, muscle, nerve, heart, liver, bone and blood. The potential of ESC to grow into specialized cells attracts enormous interest for research and disease treatment using these cells. The clinical application of stem cells involves harvest of the cells and transplantation of cells into failing organs to restore the function of the organs with or without prior in vitro differentiation.

Bone marrow stromal/stem cells (BMSC) are multipotent cells with unique biological properties and the potential to regenerate tissue and organ systems. BMSC are capable of differentiating into different cell types, including but not limited to, heart (Orlic et al., *Nature* 410:701 (2001)), lung (Krause et al., *Cell* 105:369 (2001)), liver (Petersen et al., *Science* 284:1168j (1999)), neural cells (Mezey et al., *Science* 290:1779 (2000)), skeleton muscle (Qu-Petersen et al., *Cell Biol.* 157:851 (2002)), bone (Ferrari et al., *Science* 279:1528 (1998) and Holy et al., *J Biomed Mater Res.* 65:447 (2003)), cartilage (Mackay et al., *Tissue Eng.* 4:415 (1998)) and skin (Badiavas et al., *J Cell Physiol.* 196:245 (2003)). Additionally, the use of BMSC as an alternative cell source for tissue engineering avoids the ethical issues associated with the use of embryonic tissues.

Therefore, there is a need felt within the art to identify a method of tissue engineering which will provide a functional seeded urinary tract tissue graft composition for consistently and reliably repairing damaged urinary tract tissue, including identifying alternative cell sources for use in such tissue engineering, thereby overcoming the disadvantages and defects of the prior art.

SUMMARY OF THE INVENTION

The present invention relates to materials for repairing or augmenting tissues and methods for using same. More particularly, the present invention is related to a method for providing a urinary tract tissue graft composition, as well as the urinary tract tissue graft composition produced by such method. Such urinary tract tissue graft composition includes a segment of small intestinal submucosa and at least one stem cell type seeded on a surface of the segment of small intestinal submucosa. The urinary tract tissue graft composition may further include at least one cell type selected from the group consisting of smooth muscle cells and urothelial cells, wherein the at least one cell type is also seeded on a surface of the segment of small intestinal submucosa.

Broadly, the method of the present invention includes providing a segment of small intestinal submucosa having mucosal and serosal surfaces and isolating and culturing at least one stem cell type from a tissue specimen of a subject, followed by seeding the at least one stem cell type on a surface of the segment of small intestinal submucosa. The method may further include isolating and culturing at least one cell type selected from the group consisting of smooth muscle cells and urothelial cells from a tissue specimen of a subject, and seeding the at least one cell type on a surface of the segment of small intestinal submucosa. In yet another embodiment, the method may include providing a tissue culture frame and positioning the segment of small intestinal submucosa in the tissue culture frame such that the segment of small intestinal submucosa is suspended and held in a taut position by the tissue culture frame prior to seeding of the cells thereon.

The present invention is also directed to a method for repairing a damaged urinary tract tissue of a subject. The method includes the steps required to produce the urinary tract tissue graft composition described above, followed by allowing the segment of small intestinal submucosa having the one or more cell types seeded thereon to mature in culture such that the cells exhibit three dimensional growth and matrix penetrance. The damaged urinary tract tissue is then contacted with the seeded segment of small intestinal submucosa under conditions such that growth of the urinary tract tissue occurs and the damaged urinary tract tissue is repaired, thereby restoring urological function.

An object of the present invention is to provide a method for providing a urinary tract tissue graft composition.

Another object of the present invention, while achieving the before-stated object, is to provide a seeded urinary tract tissue graft composition.

Another object of the present invention, while achieving the before-stated objects, is to provide a method for repairing a damaged urinary tract tissue of a subject.

Other objects, features and advantages of the present invention will become apparent from the following detailed description when read in conjunction with the accompanying drawings and appended claims.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 6 demonstrates the phage contrast microscopic appearance of cultured dog BMSC (A) and bladder SMC (B). Both types of cells have a similar pattern in appearance and morphology (magnification ×100).

FIG. 11 illustrates detection of bone-marrow-derived SMC grown on SIS scaffolds with intense cell penetration on day 28. (A). Masson Trichrome Staining, (B) Immunohistochemistry photomicrographs with α-SM actin staining, and (C) Immunocytochemistry staining with enhanced green fluorescent protein marker on BMSC grown on SIS.

DETAILED DESCRIPTION OF THE INVENTION

Figure 1:
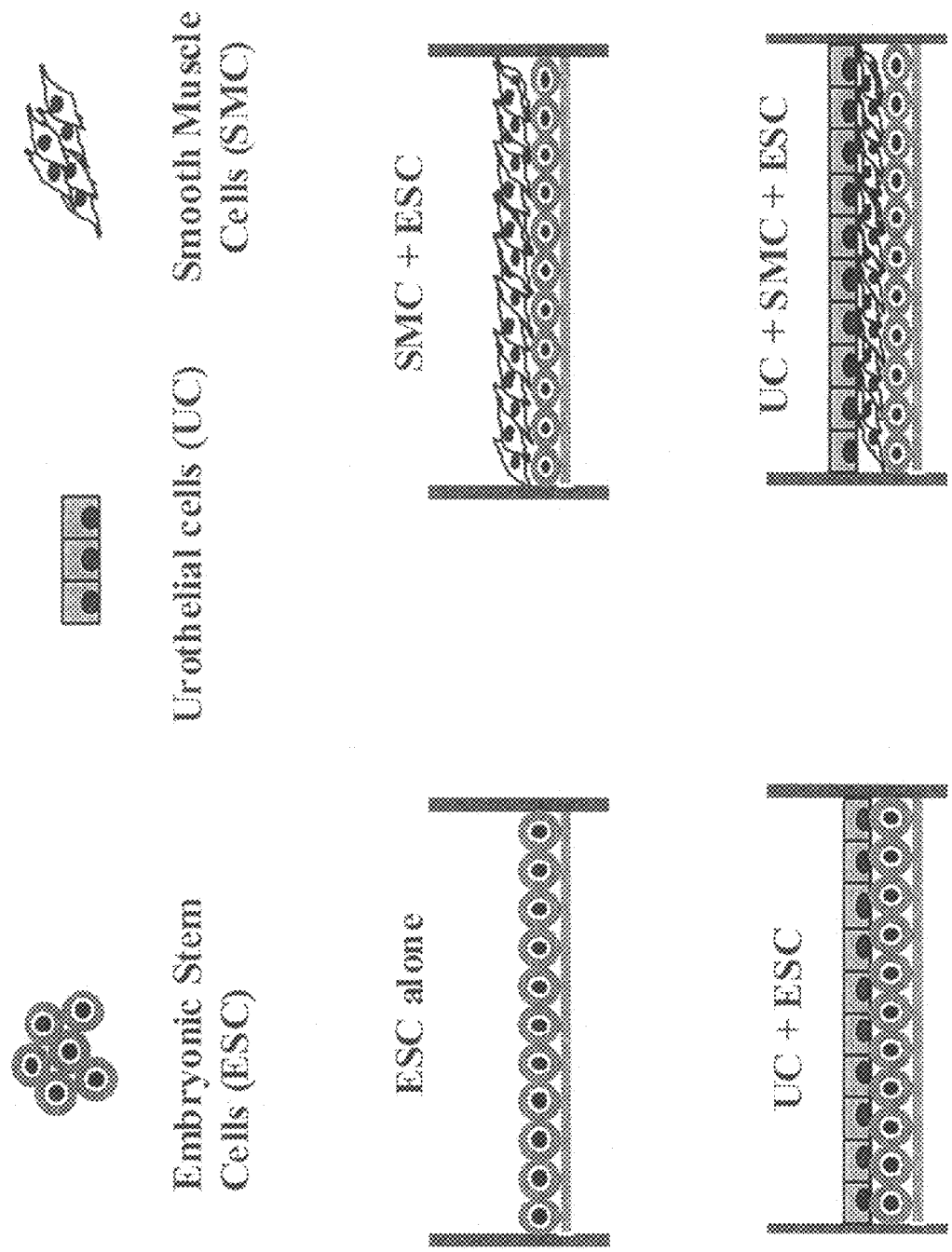
FIG. 1 is a representational diagram illustrating in vitro growth of ESC and bladder cells cultured on SIS in different culture patterns.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

One embodiment of the present invention is related to a method of producing a urinary tract tissue graft composition which closely resembles the architecture of normal tissue. Such urinary tract tissue graft composition comprises a xenograft of biodegradable porcine small intestinal submucosa (SIS) seeded with autologously obtained stem cells, alone or co-cultured with smooth muscle and/or urothelial cells, to regenerate urinary tissue and restore normal urinary function. The SIS is preferably a distal ileal segment of SIS.

The use of SIS in the method of the present invention is considered to have enhanced regenerative potential over the prior art use of PAP. SIS has been shown to have a rich supply of growth factors that have been shown in vitro to support the growth and differentiation of bladder cells. PAP lacks these factors. In addition, a much larger number of cells would be required to seed a segment of PAP compared to the same size segment of SIS. Therefore, SIS should provide a better environment and framework for the regenerative process, and therefore overcomes the defects and disadvantages of the prior art.

A polymeric nonextractable, autoclave sterilizable tissue culture frame developed for use in the SIS-supported autoaugmentation protocol for production of the urinary tract seeded tissue graft composition of the present invention has been described in copending application U.S. Ser. No. 10/013,270, filed Dec. 10, 2001, the contents of which are hereby expressly incorporated herein by reference in their entirety.

The method of the present invention involves isolation and culture of stem cells, such as embryonic or adult stem cells, from a specimen by collagenase digestion of the tissues. That is followed by seeding of the stem cells alone or in combination with bladder smooth muscle cells and/or urothelial cells at a density in a range of from about $1 \times 10^4$ cells/cm$^2$ to about $1 \times 10^6$ cells/cm$^2$, and preferably at a density of about $1 \times 10^5$ cells/cm$^2$, on a surface of the segment of SIS membrane. The stem cells may be seeded with bladder smooth muscle cells and/or urothelial cells by any of the co-culture methods described in U.S. Ser. No. 10/013,270, which has previously been incorporated by reference herein.

The term "stem cell", as used herein, refers to an undifferentiated cell that is capable of giving rise to one or more differentiated cell types. Stem cells may be unipotent or pluripotent. The terms "multipotent" or "pluripotent" may be used interchangeably herein and will be understood to refer to an undifferentiated cell that is capable of giving rise to two or more differentiated cell types. Unipotent cells only give rise to cells that will follow a particular developmental pathway and produce a single type of differentiated cell.

The present invention further includes a method for repairing a damaged or diseased urinary tract tissue of a subject. The method involves isolating and culturing at least one stem cell type from a specimen. The stem cells are then seeded on a segment of small intestinal submucosa alone or in combination with bladder smooth muscle cells (SMC) and/or urothelial cells (UC) by any of the co-culture methods described in U.S. Ser. No. 10/013,270, which has been previously incorporated by reference herein. The seeded segment of small intestinal submucosa is allowed to mature in culture and then contacted with the damaged urinary tract tissue under conditions such that growth of the urinary tract tissue occurs and the damaged urinary tract tissue is repaired, thereby restoring urological function.

One urinary trac tissue graft composition that may be utilized in accordance with the present invention comprises a distal ileal segment of SIS isolated from a mature adult pig, as described in copending application U.S. Ser. No. 10/314,799, previously incorporated herein. The term "distal ileal segment of SIS" is defined herein as a segment of small intestinal submucosa selected solely from the distal segment of the ileum and wherein the distal ileal segment has been isolated away from the duodenum, the jejunum and the proximal ileum of the small intestine, and wherein the distal segment was located within about 300 cm of the terminal ileum and closely associated with Peyer's patches, although Peyer's patches were not included in the segment. Such urinary tract tissue graft composition may be utilized in a method of repairing a damaged or diseased urinary tract tissue by promoting growth of endogenous urinary tract tissues having a urine impermeable layer and a functional muscle layer. The method includes surgically removing the damaged or diseased portion of urinary tract tissue, seeding the tissue graft composition described above with stem cells (alone or in combination with smooth muscle and/or urothelial cells), and replacing the removed portion of urinary tract tissue with the seeded tissue graft composition, and wherein replacing the removed portion of urinary tract tissue with the seeded tissue graft composition results in promoting the growth of endogenous urinary tract tissues or similar tissues while reducing the possibility of calcifications or stone formations as well as preventing any substantial reduction in graft size.

The following examples illustrate the practice of the preferred embodiments of the present invention. However, the present invention is not limited to the examples set forth.

MATERIALS AND METHODS

Isolation and culture of human bladder urothelial cells (UC) and smooth muscle cells (SMC). Human bladder tissues were obtained from open surgery for vesicoureteral reflux, ureteropelvic junction obstruction and duplex collecting system. Bladder mucosa was separated from the serosa layers, minced into 0.5 $mm^2$ pieces, and digested with 0.1% collagenase IV for 1 hour. The mucosa tissues were dissociated into single or cluster of UC following collagenase digestion. UC were then seeded on T25 plastic flasks in keratincyte serum free medium (KSFM) supplemented with epidermal growth factor (5 ng/ml), bovine pituitary extract (50 mg/ml), and cholera toxin (30 ng/ml). Bladder SMC were obtained from the rest of the bladder tissues and digested in the collagenase solution to produce a single cell suspension. SMC were then cultured in M199. The cells were incubated and maintained in a humidified cell incubator with 5% $CO_2$ air atmosphere at 37° C.

Isolation and culture of mouse embryonic stem cells (ESC). Alan Bradley 2.2 ESC (AB 2.2 cell line) derived from 129/SvEv mice embryos were provided by INCYT (Newark, N.J.) and maintained in the laboratory. To maintain ESC, culture dishes were coated with 0.1% gelatin in PBS. ESC were cultured on lethally-irradiated embryonic fibroblasts in Dulbecco's Modification of Eagle's Medium (DMEM) supplemented with 20% fetal calf serum (FCS), 2 mM L-glutamine, 100 U/ml penicillin, 1 mg/ml streptomycin, 0.1 mM non-essential amino acids, 0.1 mM deta-Mercaptoethanol, and 1:10,000 dilution of leukemia inhibitory factor (LIF).

ESC, SMC and/or UC seeded on SIS. SIS devices provided by Cook Biotech (West Lafayette, Ind.) were fashioned into small discs and used as an insert for in vitro experiments. The discs were created by suspending SIS, with the lumenal side up, over a circular (1 cm in diameter) polypropylene frame. The cultured cells were then seeded on the mucosal surface of the SIS membrane at a density of $1\times10^5$ cells per $cm^2$, incubated at 37° C. in a humidified atmosphere maintained at a 5% level of $CO_2$ and then harvested at 14 days. Four separate culture methods were evaluated (FIG. 1):

1) ESC alone, seeded on the luminal surface of SIS in DMEM with 20% FBS.
2) Layered co-culture of SMC and ESC on the luminal surface of SIS in M199.
3) Layered co-culture of UC and ESC on the luminal surface of SIS in M199.
4) Layered co-culture of SMC, UC and ESC on mucosal layers one hour after the seeding of ESC on SIS matrix in the media containing 1:1 mixture of KSFM (keratinocyte serum free medium) and M199.

Cell growth on SIS was assessed at 3, 7, 14, and 28 days after seeding and compared to growth on conventional tissue culture plates. Three replicates were prepared for the disc format for each group at each time point; each cell type was seeded at a density of $10^5$ cells/$cm^2$ SIS. Once the cells were seeded on the SIS membrane, media were replaced daily. Layered co-culture of ES cells with bladder cells on SIS were maintained in a mixture media of M199 and KSFM for 3, 7, 14 and 28 days, respectively. Each type of cell was seeded at $10^5$ cells/$cm^2$. Phenotypic differentiation of ESC was determined histologically using cell type specific markers.

For histological examination, the SIS membrane was harvested and fixed in 10% neutral buffered formalin over 24 hours followed by embedding with 4% agar to preserve cell integrity and architecture of the cell-composite membrane. The sections were used for hematoxylin-eosin (H&E) and immunohistochemical staining for alpha-smooth muscle ($\alpha$-SM) actin for SMC. To identify the cell types in the co-culture system, the cells were stained with $\alpha$-SM actin. Additionally, cells were examined with Masson trichome staining to evaluate the cell penetration into the SIS matrix.

Isolation and culture of bone marrow stromal cells (BMSC). Approximately 10-15 ml of bone marrow was obtained from the femurs of anesthetized dogs (n=5) by needle aspiration and collected in heparinized 50 ml test tubes. Bone marrow cells were diluted with 15 ml of fresh serum-free medium 199. Thirty ml total of bone marrow cell suspension was added over 10 ml of Ficoll-Paque® (Amersham Pharmacia Biotech AB, Uppsala, Sweden) and centrifuged at 400×g for 35 minutes. Mononuclei cells were collected from the bone marrow interphase. Bone marrow cells were plated in the modified medium 199 with 10% fetal bovine serum (FBS). Smooth muscle cells (SMC) were harvested from bladder biopsies on the same dog simultaneously and cultured in M199 to set up a control cell line. Cells were cultivated at 37° C under 5% $CO_2$. Medium was changed every other day until the cells reached 95% confluent.

BMSC contractility in vitro. Methods of the collagen lattice contraction assay were performed as previously reported (Kropp et al., *J Urol.* 162:1779 (1999), the contents of which are hereby expressly incorporated herein by reference in their entirety). Confluent cultures of dog BMSC from two passages were detached from flasks with 0.01% EDTA-0.05% trypsin and then mixed with soluble stabilized type I collagen. Cell concentration of BMSC is $1.5\times10^5$ cells/ml to create a cell-collagen solution. The final collagen concentration in the lattices was 0.65 mg/ml. BMSC were cultured within the collagen lattices. A 250 µl drop of the cell-collagen solution was placed onto a 35-mm diameter dry plastic dish to ensure that the lattice would remain attached for the 5 day culture period.

The cell-collagen lattice was mechanically released from the underlying plastic substratum 5 days after culture. The diameters of the cell-collagen lattices were normalized due to variation in the initial diameters of the lattices before releasing. The relative lattice diameter was obtained by dividing the diameter of the collagen lattice at each time point by the initial diameter of the lattice. The 10 minute time period was used for comparison of the relative amount of contraction for the different lattices. Each experiment was comprised of at least three cell-collagen lattices. BMSC-collagen lattices which were released in M199 with 10% FBS served as a positive control. For the negative control, BMSC-collagen lattices were released under serum free conditions after being washed twice with serum free media 199. Contractile response to Ca-ionophore A23187 ($10^{-5}$ M) was performed in a similar manner and was added to the serum free media immediately prior to lattice release.

Western Blotting. To prepare protein samples for Western blot analysis, BMSC and bladder SMC derived from the same dog were seeded in 100 mm tissue culture plates and harvested separately when cells reached about 70-80% confluence. Cells were lysed with lysis buffer consisting of 10 mM Tris-HCl (pH 7.4), 150 mM NaCl, 5 mM EDTA, and 1% (v/v) Triton X-100 in the presence of proteinase inhibitor cocktail (Complete™; Roche) at the volume of 100 ml/1×$10^6$ cells and incubated on ice for 20 min. Supernatants were cleared by centrifugation at 12,000×g for 20 min at 4° C., transferred to fresh tubes, and stored at −80° C. until use. Protein concentration was determined using the BCA Protein Assay reagents (Pierce). A total of 20 μg cellular protein from each sample was loaded onto 10% SDS-PAGE gel for α-smooth muscle (SM) actin. The proteins were then transferred to PVDF membranes (NEN Life Science) using a semi-dry transfer apparatus (Bio-Rad). After blocking the membranes in 5% non-fat dry milk (Bio-Rad) in TBST (25 mM Tris-HCl, pH 8.0, 125 mM NaCl, 0.05% Tween 20) for 1 hour at room temperature, the membranes were probed with 1:400 dilution of mouse anti-human α-SM actin in blocking reagent at 4° C. overnight. The membranes were then incubated with peroxidase-labeled affinity purified goat anti-mouse IgG secondary antibody (KPL) at 1:3000 dilution for α-SM actin at room temperature for 1 hour. The presence of protein bands were detected by the Enhanced Chemiluminescence Assay kit (Pierce).

Immunohistochemistry staining. Immunofluorescence staining of BMSC and bladder SMC were performed on those cells cultured on cover-slips. Monoclonal primary antibodies utilized in this study included α-SM actin (1:1000 dilution), desmin (1:20), SM myosin (1:100). Following fixation, cells were routinely stained as previously described (Kropp et al., *J. Urol.* 162:1779 (1999) previously incorporated by reference herein). The secondary antibody utilized for fluorescence was rhodamine-conjugated goat IgG fraction to mouse immunoglobulins. The cells were also double stained with the nucleic acid stain DAPI (4',6-diamidino-2-phenylindole, HCL) to assist in estimating the percentage of positive stained cells within a given population.

BMSC labeled with human enhanced green fluorescent protein (EGFP). Cultured BMSC were stably transfected with an expression construct containing EGFP carried by a retroviral vector (pLPCX-EGFP; Clontech). The retroviral reporter gene construct was used to produce retroviral packaging cells. Embryonic human kidney cells (GP2-293, Clontech) were transfected with virus containing EGFP cDNA and cultured in DMEM with 10% BFS and 1% sodium pyruvate for 48 hours. To transfect the packaging cell line, GP2-293 cells were seeded in tissue culture plates, and each transfection was performed at 60% cell confluence by mixing 10 mg of the PLPCX-EGFP plasmid DNA with an appropriate volume of Superfect transfection reagent (Qiagen) recommended by the manufacturer. At 48 hours following transfection, selection of stable virus-producing GP2-293 cell lines were initiated by the addition of an appropriate concentration of puromycin (Sigma) into the culture medium. Following 1-2 weeks in culture, healthy and puromycin resistant colonies were transferred to individual plates and expanded. Drug resistant clones were confirmed by Northern blot analysis using [$^{32}$P]ATP radiolabeled EGFP probe. GP2-293 virus producing cells received high glucose DMEM supplemented with 10% FCS plus 2.4 mg/ml of neomycin.

Genetically modified BMSC were generated by infecting the cells with media containing the pLPCX-EGFP construct collected from stably transfected GP2-293 cells. For retroviral infection, 1×$10^6$ BMSC were plated onto tissue culture plates overnight and exposed to virus-containing medium. After two days, an optimal concentration of neomycin determined from a kill curve was added to the medium to select cells that have integrated the viral DNA. Neomycin resistant BMSC were isolated, transferred to individual plates for expansion, and confirmed for EGFP expression using fluorescence microscopy. Stable transfection was used to ensure 100% BMSC expressing the EGFP.

BMSC seeded on SIS. BMSC were implanted and grown on commercially available SIS cell culture disks (VivoSIS™ Inserts, COOK®). The disks were placed in a 12 well culture plate and then filled with culture medium six hours after implanting of cells. Air bubbles were removed from the bottom of disks. The cells were then seeded onto SIS for 3, 7, 14 and 28 days. EGFP transfection was checked while BMSC growth progress on non-transparent SIS was visualized under a fluorescence microscope.

The cell-SIS constructs were harvested and embedded in paraffin overnight. The slides were cut in sections 5 μm thick and submitted for immunohistochemical staining. For detecting the EGFP-labeled cells, the primary antibody was chicken anti-GFP (Chemicon) at a concentration of 1:500. The secondary antibody was donkey anti-chicken (Chemicon) at a concentration of 1:2000. Control slides received PBS in place of the primary antibody. The immunostained sections were then observed and photographed with the microscope.

RESULTS

Figure 2:
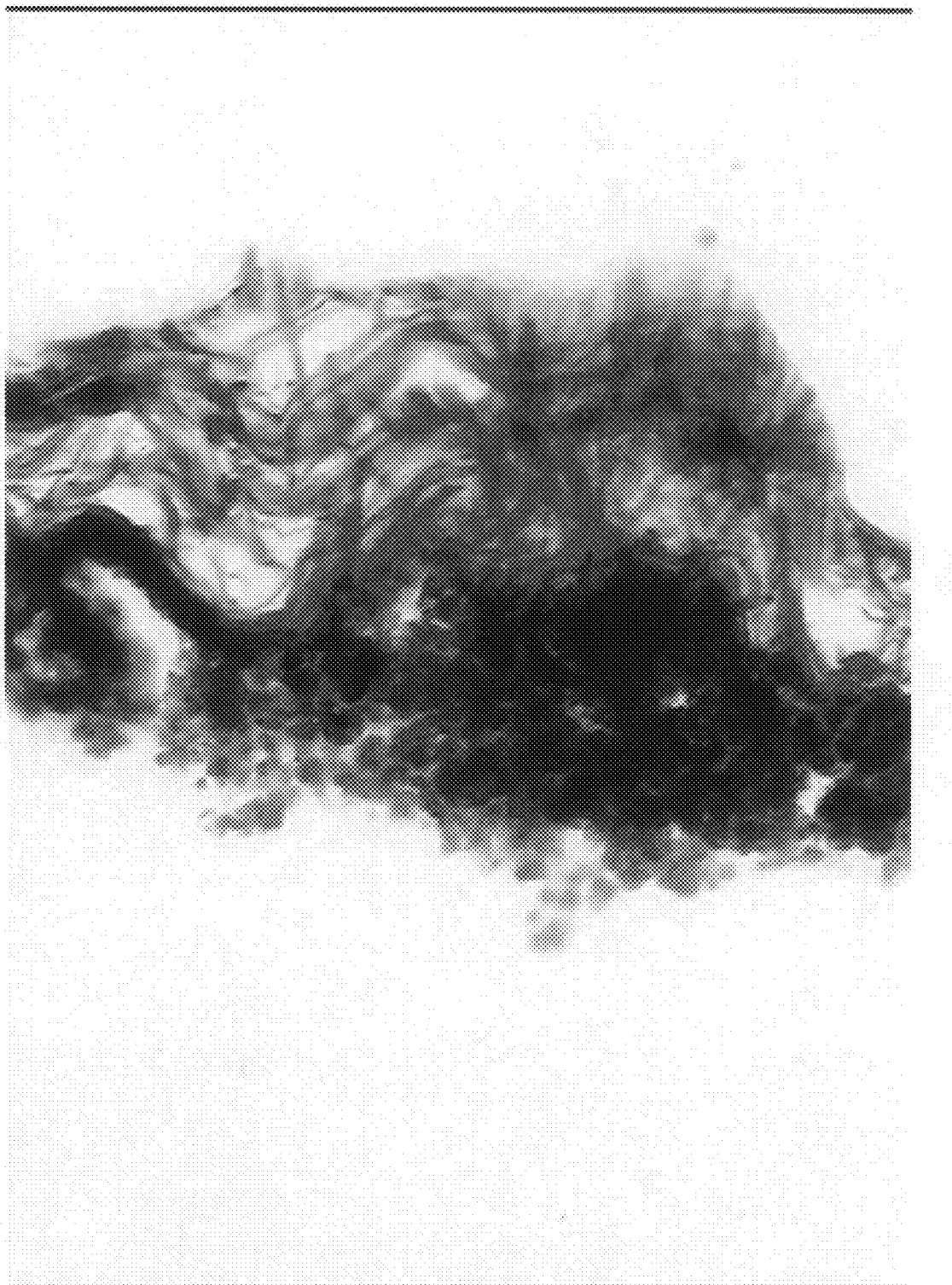
FIG. 2 is a photomicrograph illustrating Masson's trichrome staining of ESC cells (red) seeded alone on SIS (blue) (magnification ×62.5).

ESC seeded on SIS. When seeded alone, ESC readily adhered to SIS and grew in an organized fashion in three dimensions and in several cell layers with minimal penetration into the SIS matrix (FIG. 2). However, ESC did not demonstrate expression of α-SM actin using immunohistochemical staining at any period of time investigated.

Figure 3:
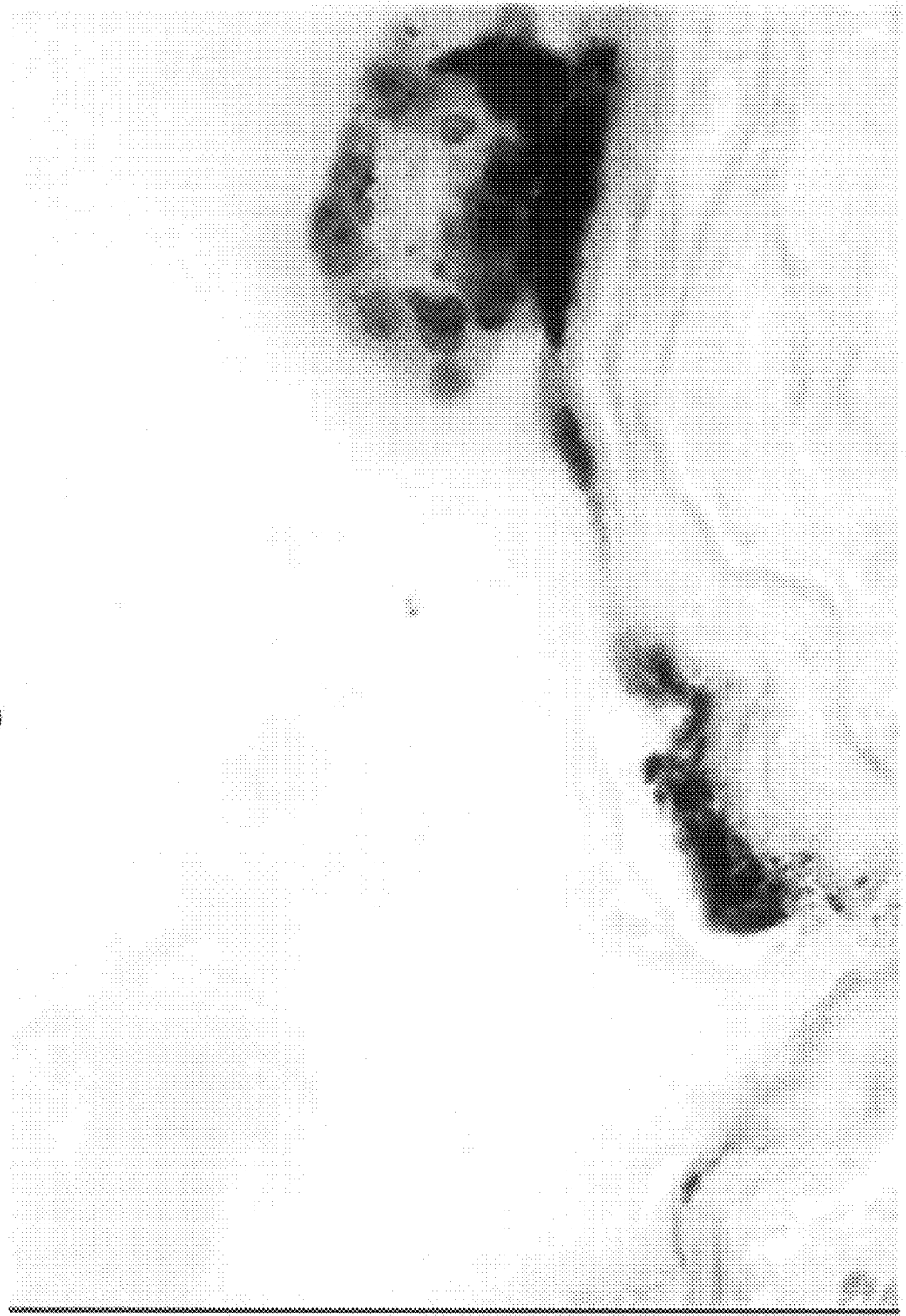
FIG. 3 is a photomicrograph illustrating that when ESC and bladder UC were co-cultured on SIS, certain cells stained positive for alpha-smooth muscle (α-SM) actin (Brown).

When ESC were recombined with human bladder UC on SIS in M199 for two weeks in vitro using the co-culture technique, there appeared to be a synergistic effect with regard to enhanced growth and penetration of the cells into the SIS membrane. In addition, there were certain cells that stained positive for α-SM actin (FIG. 3).

Figure 4:
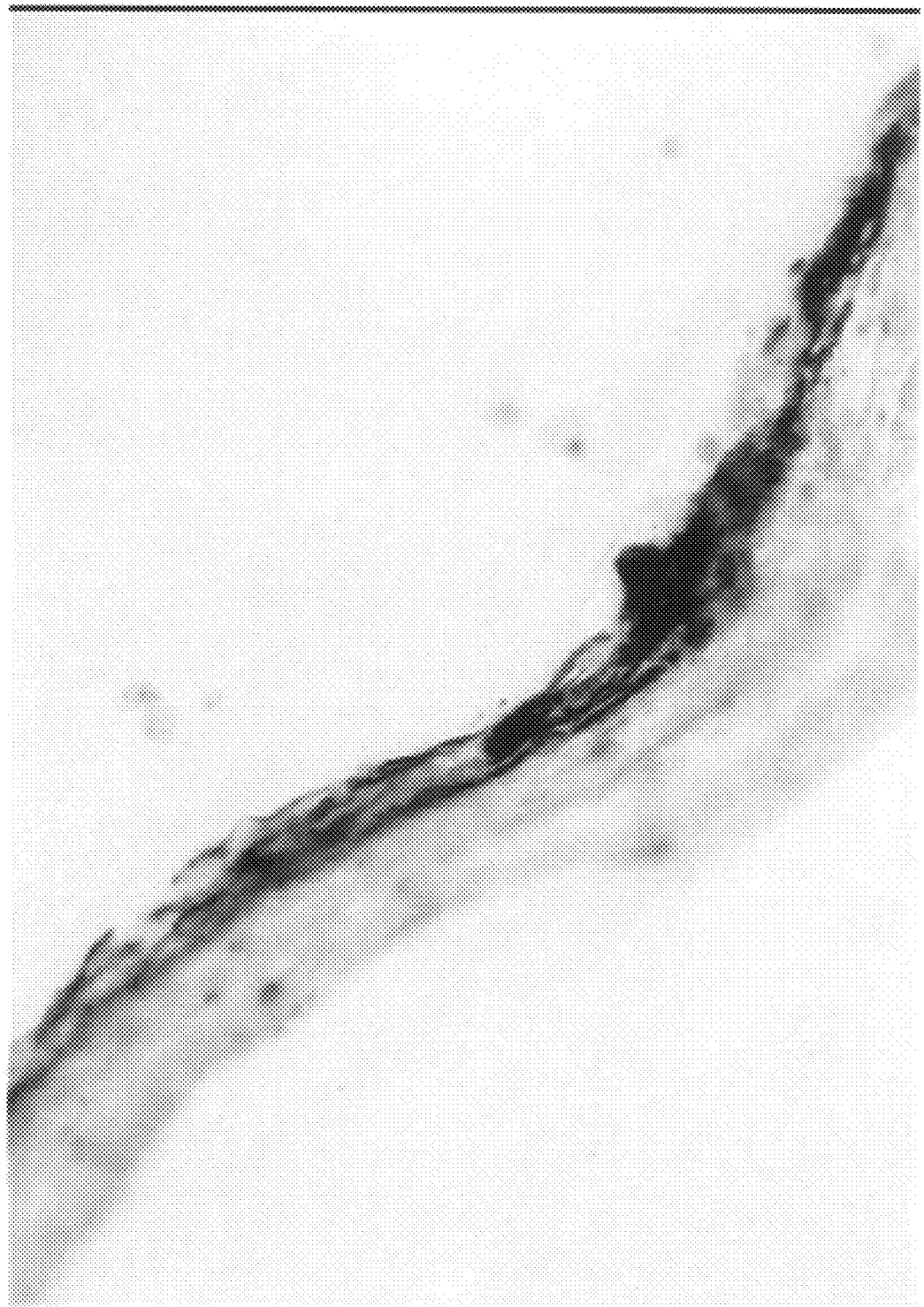
FIG. 4 is a photomicrograph demonstrating that when ESC and SMC were co-cultured on SIS, the majority of the cells stained positive for α-SM actin (Brown).

When ESC and SMC were seeded together in a "layered" fashion, the cells rearranged themselves in a fashion such that both types of cells were basally located with SIS matrix penetrance. However, it is impossible to distinguish ESC from SMC. In this co-culture pattern, there was also definite enhancement of the cells layered growth pattern and SMC penetration of the matrix. Identification of individual cell types in the layered and mixed co-cultures was achieved with immunohistochemical analysis for α-SM actin (FIG. 4).

Figure 5:
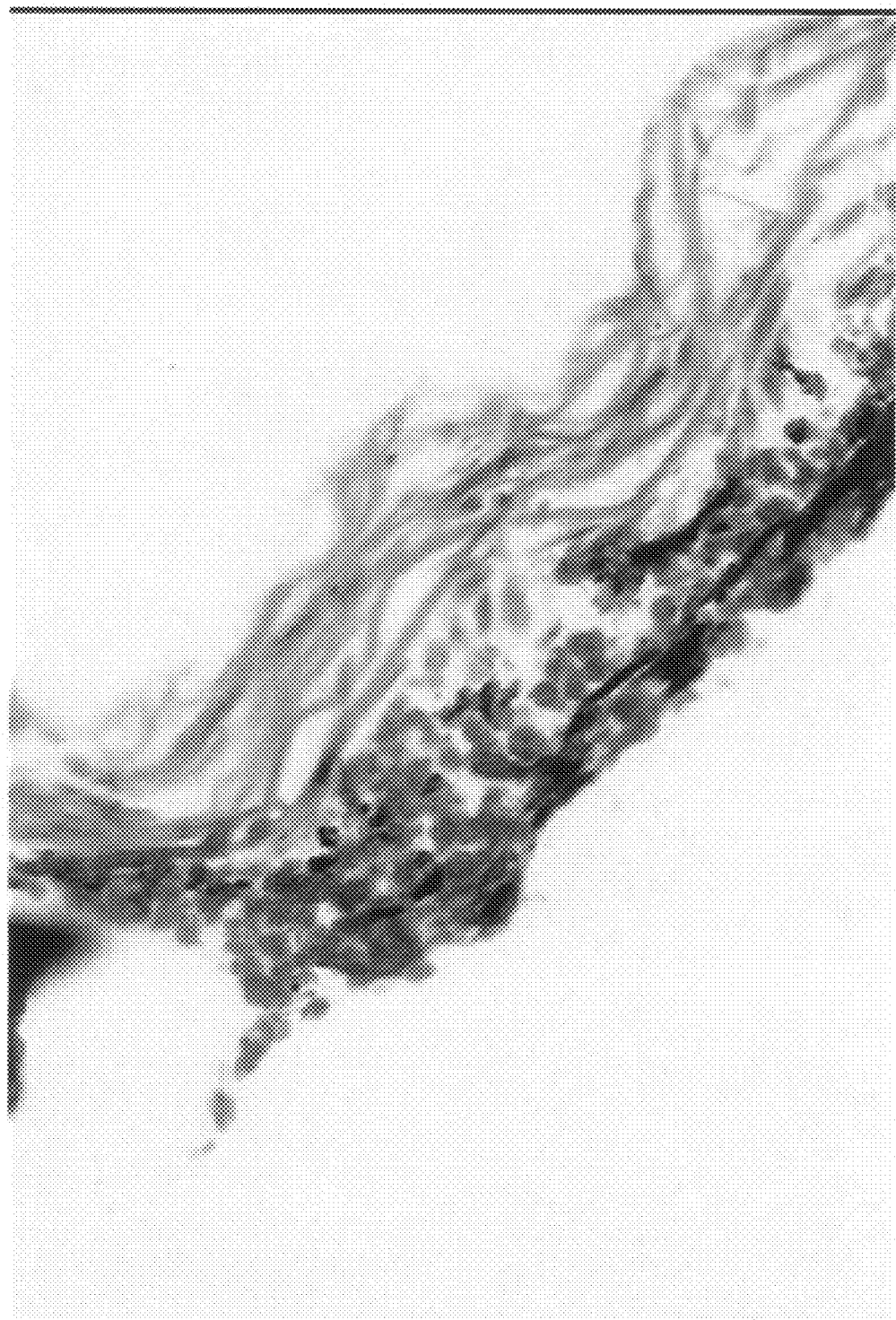
FIG. 5 is a photomicrograph of a Masson's trichrome stained section of co-culture of ESC, SMC and UC on SIS, demonstrating enhanced matrix penetration by the cells.

When ESC, SMC and UC were co-cultured, the cells appeared more readily adhered to the SIS and gave rise to better three-dimensional architecture with more diffuse bundles of SMC (FIG. 5). The majority of the cells were α-SM actin positive.

Isolation and culture of BMSC. Primary culture of BMSC was successfully established from a simple aspiration technique. In the first two days after Ficoll-Paque® isolation, BMSC generated from single-cell suspensions of marrow and started to grow in colonies. Each colony formed foci of four to six cells under the microscope (FIG. 6A). The bone marrow cells in the foci remained dormant for 5 to 7 days and began to multiply rapidly to form uniform spindle shaped-like cells (FIG. 6B), morphologically being similar to fibroblasts or SMC in vitro. However, BMSC showed more proliferative potential and grew more rapidly than the bladder SMC at the first three generations. BMSC proliferation slowed down after passage 4, compared with the bladder SMC being able to passage up to 10 generations.

Figure 8:
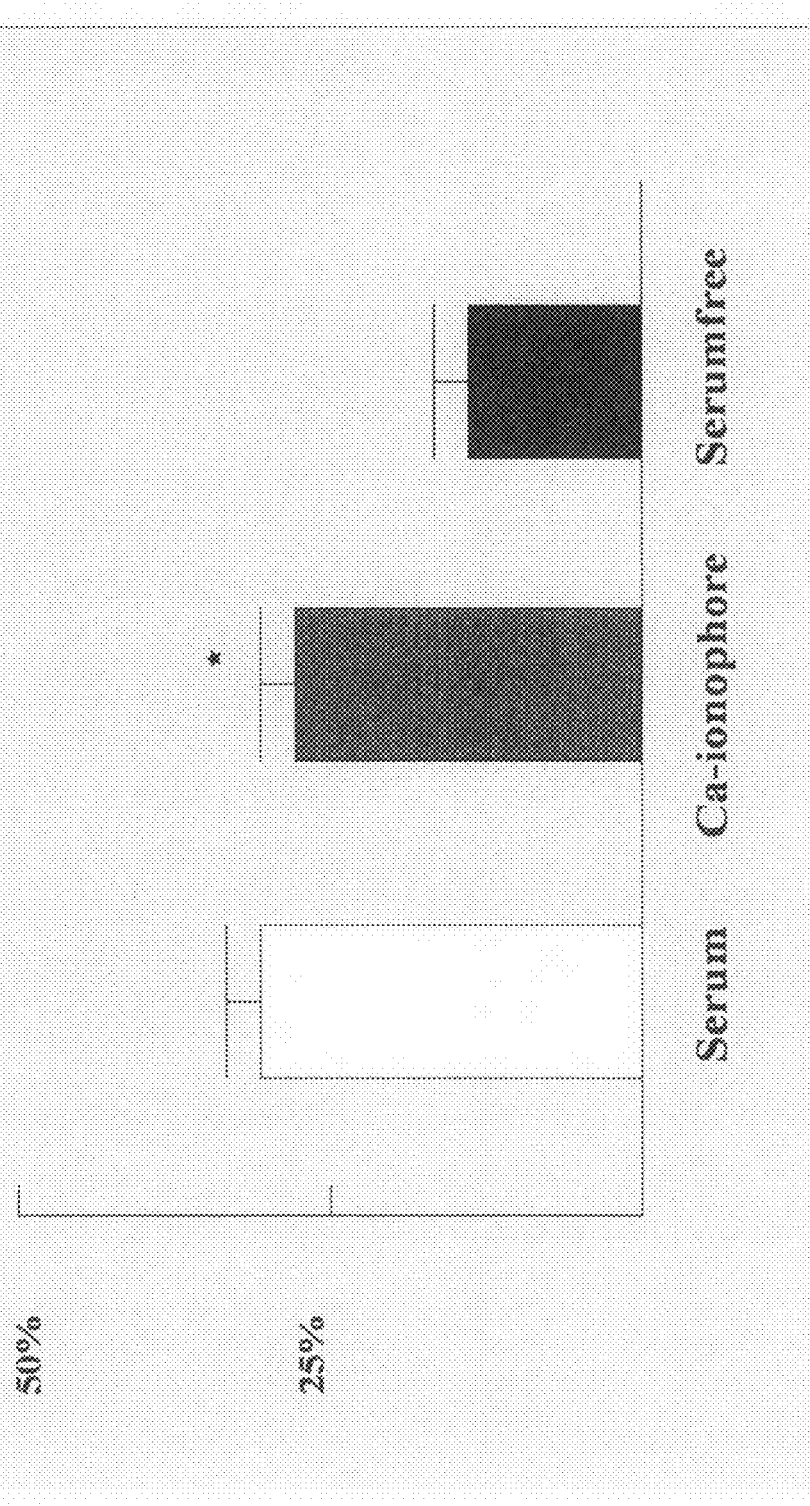
FIG. 8 demonstrates an evaluation of BMSC in vitro contractility with collagen type I lattice assay. BMSC have significantly more contractile response to a calcium-ionophore (36% ±2) and 10% fetal bovine serum (37% ±1), but less contraction to serum free (0.20% ±1) 10 minutes after release of lattices.

BMSC-collagen contractility assay. Prompt contraction appeared following the release of attached BMSC-collagen lattices in the absence of serum as a positive control, which reduced the lattice diameter within the first 10 minutes after releasing. In the presence of serum, the relative percent contraction was 37±1%. In the serum-free condition as a negative control, the relative percent contraction was 20±1%. In the presence of 10 mM calcium-ionophore (A23187), BMSC demonstrated a rapid lattice contraction of 36±2%. This reaction was significantly higher in relative percent contraction than that of the serum-free condition (P<0.01) (FIG. 8).

Figure 7:
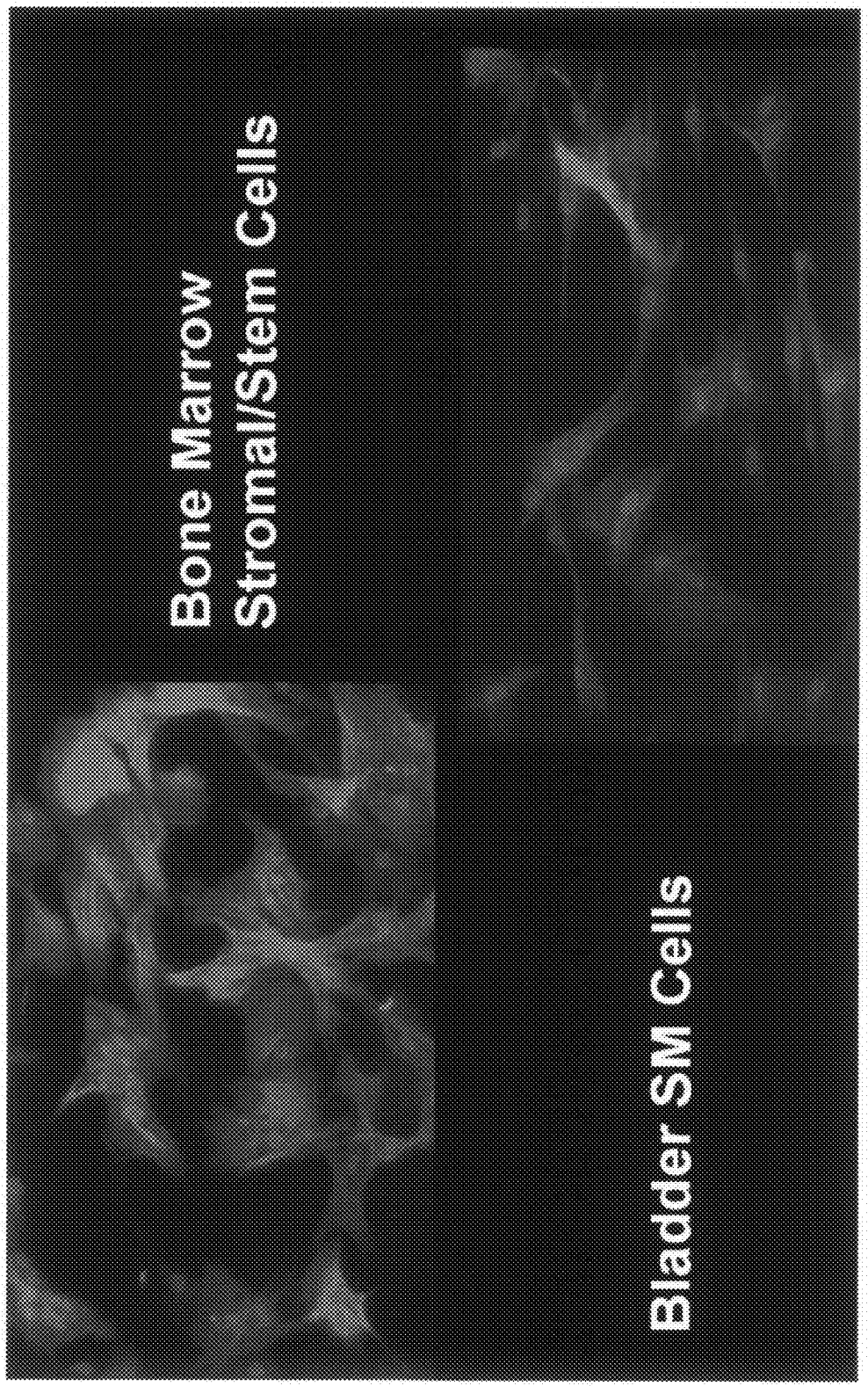
FIG. 7 is a photomicrograph of cultured BMSC (A) and bladder SMC (B) double stained with α-SM actin and nucleic acid stain DAPI. Nuclear labeling with DAPI is shown in blue and α-SM actin expression is shown in red. Both cell types were positive for α-SM actin expression.
Figure 9:
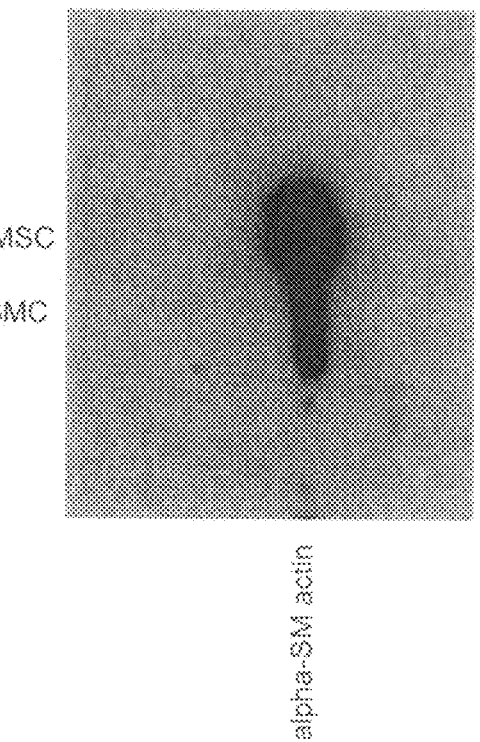
FIG. 9 is a Western blot analysis of α-SM actin. Cellular proteins extracted from cultured BMSC and bladder SMC were size separated by SDS-PAGE gel and transferred to PVDF membranes for detection of α-SM actin expression using antibodies raised against this molecule. Similar patterns of α-SM actin expression was observed in these two cell populations.

Immunohistochemistry staining and Western Blotting. Immunohistochemical staining of the cultured BMSC for a SMC marker and nuclei acid stain showed that over 95% cells stained for α-SM actin. BMSC expressed outstandingly apparent α-SM actin, labeled with thick filaments in the cytoplasm. Those cells showed more vigorous expression of α-SM actin than bladder SMC (FIGS. 7A-7B). This phenomenon of α-SMA positivity in the cultured BMSC was further confirmed using Western blotting. Western blot analysis was also performed for α-SM actin expression in BMSC, and the expression level of this molecule was higher in BMSC than that in the SMC (FIG. 9). However, none of the BMSC stained positive for both desmin and SM myosin antibodies, while SM myosin and desmin expression were both consistently present in SMC derived from dog bladder when the cells grew on the cover-slips (Table 1).

TABLE 1

Smooth muscle markers of dog bone marrow stromal cells cultured with immunohistochemistry

| Cell Lines | Dog BMSC | Dog bladder SMC |
|---|---|---|
| Alpha-SM actin | ++++ | ++ |
| Desmin | − | + |
| SM myosin | − | + |

Figure 10:
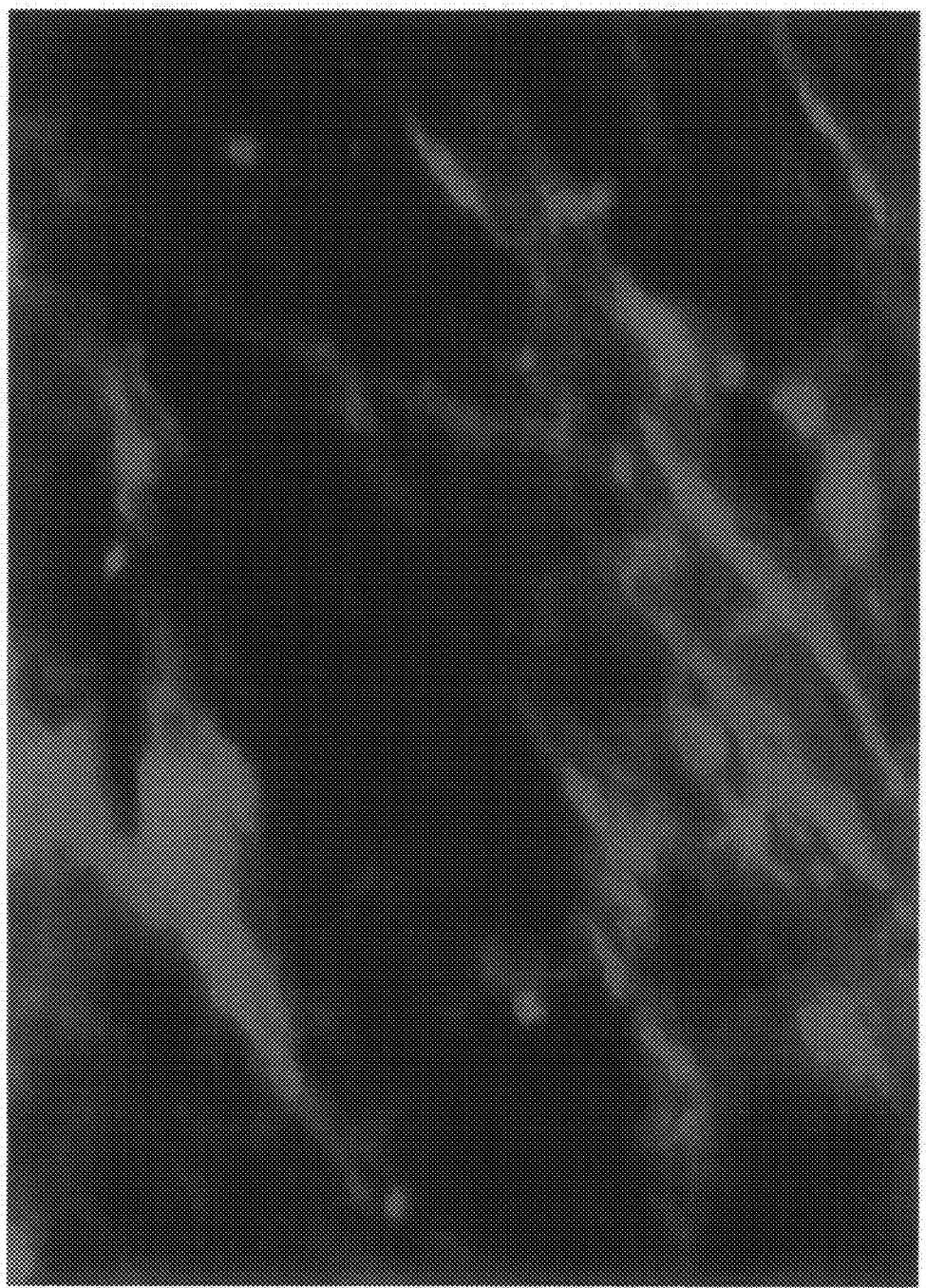
FIG. 10 are Fluorescence photomicrographs of dog BMSC cultured on SIS membrane, detecting enhanced green fluorescent protein (EGFP) expression in green.

BMSC transfected with EGFP showed strong green fluorescent protein label on the cover-slips. The growth pattern of BMSC is in an identical fashion as the non-transfected BMSC. On the seeded SIS sheet, EGFP expression for BMSC remained visible for four whole weeks (FIG. 10).

Differentiation of BMSC in SIS matrix. Histologically, there were 1-2 cell layers of BMSC attached on SIS by day 3. Continuous incubation of the cells on SIS resulted in the proliferation of colonies that formed more than 2 layers on the SIS surface and started matrix penetration by 7 days. There were multiple layers of cells on the surface of the SIS with evidence of matrix penetration by 14 days. The cell-seeded SIS graft eventually formed with multiple cell layers of matrix penetration by 28 days (FIG. 11A). Using immunocytochemistry, BMSC expressed positive for α-SM actin at each period of time, and the cells with positive SMC markers were observed to have matrix penetration of SIS with time. (FIG. 11B). Consistently, seeded-SIS demonstrated EGFP positive labeling at each of the time points, and labeled BMSC showed increasing matrix penetration with time (FIG. 11C).

DISCUSSION

Current strategies for engineering urinary bladder involve harvesting urothelium and smooth muscle cells from a tissue biopsy of a host bladder and seeding these cells on a degradable scaffold to enhance bladder regeneration following implantation. However, when the bladder cells are bio-chemically or physiologically abnormal, it may not be advisable to obtain the diseased cells for tissue engineering purposes. It is important to seek other cell sources to replace the diseased native bladder cells and induce regeneration of a normal-functioning bladder.

Tissue engineering in conjunction with the use of stem cells provides a promising technology in replacing pathologically-altered tissues or organs. Currently, stem cells, including embryonic stem cells, BMSC and other adult tissue-specific stem cells, are actively under investigation for tissue regeneration purposes. ESC or adult stem cells could be induced for differentiation into bladder cell lineages that can then be used for bladder tissue engineering to replace failing bladders. Since research on stem cell differentiation into bladder lineage is limited, induction of stem cell differentiation into bladder tissues in an in vitro co-culture system for bladder augmentation is the focus of the present invention.

The present invention is directed to the development of tissue engineering techniques for replacing urinary bladder following partial or total removal of bladder. As shown herein, stem cells can be a valuable cell source for promoting bladder regeneration by using stem cells seeded on SIS. Bladder UC and SMC re-differentiation in vitro has been successfully obtained following seeding on SIS in a co-culture system (see U.S. Pat. No. 7,122,200, previously incorporated herein by reference).

Due to the pluripotent potential of embryonic stem cells (ESC), the direct contact interaction of ESC to bladder UC and/or SMC may provide necessary environments in a three-dimensional culture system to drive ESC differentiation into bladder UC or SMC. Phenotypic changes in mouse ESC were induced in a co-culture system with human bladder cells. To induce ESC to differentiate into phenotypes, stem cells were either seeded on SIS individually or co-cultured with bladder UC and/or SMC. Such experiments clearly demonstrate that the combination of ESC with UC and/or SMC can re-organize themselves on SIS and re-differentiate into differentiated smooth muscle cell phenotypes. In addition, stromal-epithelial or cell-cell interaction is important for stem cell growth and differentiation, and thus embryonic stem cells may be a great potential cell source for tissue engineering.

BMSC possess superior advantages as an alternative cell source because they are easily harvested and because a large amount of cells can be achieved in vitro from a small amount of bone marrow. Those cells are also highly responsive to differential micro-environments and do not induce any immune reaction or rejection. Additionally, BMSC do not cause any conflict with ethical issues concerning stem cells because the patient's own cells are used as the cell source. Numerous investigations have shown that BMSC have great potential to regenerate different tissue and organ systems. BMSC possess the characteristics of embryonic stem cells that are capable of differentiating into various cell types, such as cardiomyocyte, bone, cartilage, adipocyte, and hematopoietic supporting tissues (see references listed herein above). The present invention presented the role of bone marrow derived SMC in replacement of bladder SMC when native bladder muscle tissues are unavailable. To demonstrate that BMSC are capable of promoting differentiation of bladder SMC-like cells, in vitro studies were performed that focused on the expression of SM biomarkers, contractile function, labeling techniques with EGFP and growth patterns of bone marrow cells on SIS matrix in vitro.

To characterize BMSC based solely on their morphology viewed through a microscope is nearly impossible since BMSC appear uniformly spindle-shaped in appearance, a very similar phenotype to other cells such as fibroblasts and bladder SMC. Therefore, SMC markers are employed to characterize bone marrow cell features. It has been shown herein that BMSC have strong α-SM actin expression. Furthermore, BMSC have also been shown to contain higher levels of α-SM actin molecular expression than bladder SMC, which was confirmed both by immunocytochemistry and Western blot analysis. BMSC did not express smooth muscle myosin and desmin. These results suggest that BMSC has a similar cellular composition to SMC even though they are not of smooth muscle tissue origin.

BMC were found to have the capacity to contract a collagen-glycosaminoglycan analog of extra-cellular matrix in vitro (Cai et al., $Tissue\ Eng.$ 7:829 (2001)). However, it is still unknown whether BMSC are more like fibroblasts or SMC. It has previously been demonstrated that SMC can be differentiated from fibroblasts based upon their different contractile responses to calcium (Kropp et al., $J.\ Urol.$ 162:1779 (1999)). SMC remarkably responds to calcium-ionophores with contractility in vitro, while fibroblasts do not. The in vitro contractile response of BMSC to several agonists known well to induce in vitro contraction of bladder SMC were characterized herein, and such experiments confirm that BMSC possess the contractility of SMC since BMSC presented a significant increase in collagen lattice contraction to calcium-ionophore compared to serum-free collagen lattice contraction. The amount of contraction of non-cultured BMSC promoted by the calcium-ionophore was similar to that observed for serum. It appears that BMSC can be manipulated in vitro to subsequently form SMC-like cells, thereby providing a powerful new cell source for tissue engineered urinary tract reconstruction.

When a cell-seeding technique is used to provide an autograft for tissue engineering, it is very important to know the origination of tissue regeneration, that is, whether the generated tissues arose from the implanted graft cells or from the native cells migrating from the edge of the wound. Enhanced green fluorescent protein (EGFP) is a common specific marker used for tumor cell migration after cell transplantation (Zagzag et al., $Brain\ Pathol.$ 13:34 (2003), the contents of which are hereby expressly incorporated herein by reference). Fluorescent protein from jellyfish is detected by direct visualization. EGFP continues to emit fluorescence after fixation in formaldehyde and formalin (Zagzag et al., $Brain\ Pathol.$ 13:34 (2003) and Chalfie et al., $Science$ 263:802 (1994), the contents of which are hereby expressly incorporated herein by reference), which makes EGFP more convenient for use as a marker to detect labeled cells in tissue blocks after implantation into the host. With the EGFP marker, graft cells are easily and clearly noticeable from their surrounding native cells. In the present invention, BMSC were successfully labeled with EGFP after transfection of the cells with cDNA plasmid in vitro. No difference in morphology, cell growth or proliferation was observed between labeled and unlabeled BMSC. Consistent appearance of GFP-expressing BMSC was seen on SIS matrix for all periods of time investigated up to 4 weeks. Transfection of BMSC with the cDNA plasmid has the advantage of recognizing graft cells in bladder regeneration. Use of gene transfer techniques for expression of a traceable marker provides a method for monitoring seeded cells in bladder regeneration processes in vivo.

SIS has been shown to be an appropriate scaffold for in vitro differentiation of UC and SMC in different culture patterns (U.S. Ser. No. 10/013,270, previously incorporated herein by reference). An intense matrix penetration of SMC was observed with layered co-culture of UC and SMC. In the present invention, BMSC grew several layers on the surface of SIS and had greater matrix penetration of cells with time, which is a similar appearance and growth pattern to that of SMC grown on SIS. Cultured BMSC consistently expressed α-SM actin at each point of time investigated, and the cells grew and penetrated into the SIS matrix. The advantage of matrix penetration is that it may protect the seeded cells from falling off or washing away from the surface of the SIS scaffold during implantation procedures, and thus the cells existing within the matrix could continue to proliferate and regenerate after implantation. The present invention demonstrates that BMSC not only play a physiological role in contractility, but also play an important role in tissue engineering and contribute to the mechanism of bladder regeneration.

Thus it should be apparent that there has been provided in accordance with the present invention a urinary tract tissue graft composition, a method of providing a urinary tract tissue graft composition, and a method for repairing a damaged urinary tract tissue of a subject, that fully satisfies the objectives and advantages set forth above. Although the invention has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the appended claims.

What is claimed is:

1. A method for repairing a damaged urinary tract tissue of a subject, comprising the steps of:
   isolating and culturing at least one bone marrow stromal cell from a tissue specimen of a subject;
   isolating and culturing at least one cell type selected from the group consisting of smooth muscle cells and urothelial cells from the tissue specimen of the subject;
   providing a segment of small intestinal submucosa having a mucosal surface and a serosal surface;
   seeding the at least one bone marrow stromal cell on a surface of the segment of small intestinal submucosa;
   seeding the at least one cell type selected from the group consisting of smooth muscle cells and urothelial cells on a surface of the segment of small intestinal submucosa;
   allowing the segment of small intestinal submucosa having the cell types seeded thereon to mature in culture such that the at least one bone marrow stromal cell differentiates into a smooth muscle-like cell and both cell types exhibit three dimensional growth and matrix penetrance; and
   contacting the damaged urinary tract tissue with the seeded segment of small intestinal submucosa under conditions such that growth of the urinary tract tissue occurs and the damaged urinary tract tissue is repaired, thereby restoring urological function.

2. The method of claim 1 wherein, in the step of providing a segment of small intestinal submucosa, the segment of small intestinal submucosa consists essentially of a distal ileal segment of small intestinal submucosa isolated from a mature adult pig.

3. The method of claim 1 wherein, in the steps of seeding the at least one bone marrow stromal cell on a surface of the segment of small intestinal submucosa and seeding the at least one cell type selected from the group consisting of smooth muscle cells and urothelial cells on a surface of the segment of small intestinal submucosa, the at least one bone marrow stromal cell is seeded on the mucosal surface of the segment of small intestinal submucosa and the at least one cell type selected from the group consisting of smooth muscle cells and urothelial cells is seeded on the mucosal surface of the segment of small intestinal submucosa.

4. The method of claim 1 wherein, in the steps of seeding the at least one bone marrow stromal cell on a surface of the segment of small intestinal submucosa and seeding the at least one cell type selected from the group consisting of smooth muscle cells and urothelial cells on a surface of the segment of small intestinal submucosa, the at least one bone marrow stromal cell is seeded on the mucosal surface of the segment of small intestinal submucosa and the at least one cell type selected from the group consisting of smooth muscle cells and urothelial cells is seeded on the serosal surface of the segment of small intestinal submucosa.

5. The method of claim 1 wherein, in the steps of seeding the at least one bone marrow stromal cell on a surface of the segment of small intestinal submucosa and seeding the at least one cell type selected from the group consisting of smooth muscle cells and urothelial cells on a surface of the segment of small intestinal submucosa, the at least one bone marrow stromal cell is seeded on the serosal surface of the segment of small intestinal submucosa and the at least one cell type selected from the group consisting of smooth muscle cells and urothelial cells is seeded on the mucosal surface of the segment of small intestinal submucosa.

6. The method of claim 1 wherein, in the steps of seeding the at least one bone marrow stromal cell on a surface of the segment of small intestinal submucosa and seeding the at least one cell type selected from the group consisting of smooth muscle cells and urothelial cells on a surface of the segment of small intestinal submucosa, the at least one bone marrow stromal cell is seeded on the serosal surface of the segment of small intestinal submucosa and the at least one cell type selected from the group consisting of smooth muscle cells and urothelial cells is seeded on the serosal surface of the segment of small intestinal submucosa.

* * * * *

UNITED STATES PATENT AND TRADEMARK OFFICE
CERTIFICATE OF CORRECTION

PATENT NO.        : 7,875,276 B2                                Page 1 of 1
APPLICATION NO.   : 11/799926
DATED             : January 25, 2011
INVENTOR(S)       : Bradley Kropp et al.

It is certified that error appears in the above-identified patent and that said Letters Patent is hereby corrected as shown below:

Column 11, line 65: Delete "PLPCX-EGFP" and replace with -- pLPCX-EGFP --.

Signed and Sealed this
Fifth Day of April, 2011

David J. Kappos
*Director of the United States Patent and Trademark Office*